United States Patent [19]

Cleeland et al.

[11] 4,178,360

[45] Dec. 11, 1979

[54] RADIOLABELLED RUBELLA VIRUS AND METHOD

[75] Inventors: Roy Cleeland, Short Hills, N.J.; Joanne Durkin, Staten Island, N.Y.; Michael J. Kramer, Glen Ridge, N.J.

[73] Assignee: Hoffmann-La Roche Inc., Nutley, N.J.

[21] Appl. No.: 886,848

[22] Filed: Mar. 15, 1978

[51] Int. Cl.$^2$ .................. G01N 33/16; A61K 43/00
[52] U.S. Cl. .................................. 424/1; 23/230 B; 424/8; 424/12
[58] Field of Search ............... 424/1, 8, 12; 23/230 B

[56] References Cited

U.S. PATENT DOCUMENTS 4,059,491  11/1977  Iwasa et al. ................ 424/12

Primary Examiner—Benjamin R. Padgett
Assistant Examiner—Christine M. Nucker
Attorney, Agent, or Firm—Jon S. Saxe; George M. Gould; Frank P. Hoffman

[57] ABSTRACT

A novel labelled antigen consisting of $^{125}$I-rubella virus and its use in a radioimmunoassay for rubella virus specific antibodies in human serum is disclosed.

5 Claims, No Drawings

RADIOLABELLED RUBELLA VIRUS AND METHOD

BACKGROUND OF THE INVENTION

A solid-phase radioimmunoassay for rubella virus specific antibodies in human serum utilizing rubella virus antigen absorbed on polystyrene balls and $^{125}$labelled second antibody (sheep antihuman IgG and IgM) was described by Kalimo et al., J. Clin. Microbiol 4, No. 2. 117 (1976).

Another procedure utilized in the art for detection of rubella is the virus hemagglutination inhibition (HI) test. A description of such procedure is presented in detail in Immunology series No. 5, Procedural guide, Public Health Service, Atlanta, pp. 57–88 (1974).

Immunofluorescent procedures are also utilized in the art. Representative disclosures of such technique are provided by the following references:

Crodock-Watson et al., J. Hyg. 70, 473 (1972);
Forgani et al., Intervirology 1, 48 (1973);
Haire and Hadden, J. Med. Microbiol, 5, 237 (1972); and
Iwatha et al., Can. Med. Assoc. J., 106, 327 (1972).

General procedures for carrying out radioimmunoassays for viral specific antibodies are provided by the following references:

Charlton and Blandford, J. Immunol. Methods, 8, 319 (1975);
Patterson and Smith, J. Clin. Microbiol, 2, 130 (1975);
Rosenthal et al., Appl. Microbiol, 26, 478 (1973); and
Smith et al., J. Immunol. Methods, 5, 337 (1974).

DESCRIPTION OF THE INVENTION

The present invention relates to a novel radiolabelled antigen $^{125}$I-rubella virus and to the use of this labelled antigen in a radioimmunoassay for detecting the presence of rubella specific antibodies in human serum specimens.

Virus hemagglutination inhibition and complement fixation tests are widely used for this purpose presently. The results obtained however are not always conclusive. This is due in part to the problem that a low HI titer observed could be due to a rubella infection or to incomplete removal of nonspecific hemagglutination inhibitors from the serums. Thus, successful use of the HI test depends in large measure on the care and technique employed in pretreating the serum samples to remove such nonspecific factors. Obviously such pretreatment procedures increase the time, cost and complexity of running the HI and CF assays.

The use of radioimmunoassay to detect the presence of rubella specific antibodies avoids the necessity of pretreating the serum samples. However, use of a solid phase radioimmunoassay such as proposed by Kalimo et al., supra where the purified virus antigen is absorbed on polystrene balls and the second antibody is radiolabelled also has serious disadvantages. First, it is quite difficult to standardize the antigen-polystyrene conjugate which can vary substantially in content from preparation to preparation. Additionally, use of a labelled second antibody requires the user to retitrate the second antibody each time it is used due to the known instability of radiolabelled antibody preparations.

In contrast to the prior art procedures, the use of the novel radiolabelled rubella virus of the present invention provides a radioimmunoassay for rubella antibodies which does not require pretreatment of the serum samples, is not subject to standardization problems with a supported antigen and does not employ unstable radiolabelled second antibody preparations.

The rubella virus used as the substrate for radioiodination is cultured and purified by procedures well-known in the art. Selection of particular strains is not critical to the practice of the invention and thus, any readily available rubella strain may be employed.

Harvested, ultrafiltered (cut-off of 10,000 molecular weight) rubella virus fluids are concentrated in buffered saline without calcium and magnesium at a pH of about 8.0 and stored at $-70°$ C.

The concentrated virus ($\sim 150$ $\mu$g/ml of protein) may then be radioiodinated by any conventional procedure for introducing $^{125}$I into a proteinaceous molecule. A suitable method that can be employed involves treatment of the virus solution with $^{125}$I and Chloramine-T using phosphate buffer pH 7.5 as the reaction medium.

Purification of the $^{125}$I-rubella virus can be carried out using procedures well-known in the art. A suitable procedure involves column chromatography through agarose beads.

The radioimmunoassay procedure employed in conjunction with the novel $^{125}$I-rubella virus antigen is not narrowly critical. Most preferably a double antibody technique will be employed. The second antibody used in such preferred procedure is prepared in a manner know per se by immunizing a suitable non-human host animal, such as a sheep, goat, horse, rabbit, donkey or the like, with human IgG. The host animal will develop antibodies to the human IgG which are isolated in the usual manner and employed as the second antibody herein. This second antibody will be immunoreactive for the first antibody (the rubella specific antibody) and will complex with it.

One suitable technique for conducting a radioimmunoassay using two antibodies involves assaying for the presence of rubella virus specific antibodies in human serum by treating the serum sample with the labelled antigen and the second antibody so as to form an insoluble conjugate between the labelled antigen, the first antibody and the second antibody. The precipitate is separated from the supernatant and the radioactivity of either the supernatant or precipitate counted and compared to a previously generated standard curve to determine the concentration of the antibody in the sample. Such technique is utilized, for example, in U.S. Pat. No. 3,974,269 to detect gonorrhea antibodies in human serum.

An improved version of such procedure is described in U.S. patent application Ser. No. 731,237 filed October 12, 1976. In such improved procedure maximum label binding and thus maximum assay sensitivity was found to occur with the use of diluted antihuman IgG in an amount sufficient to produce a non-visible agglutinate of the microbial antigen-serum antibody conjugate. It was the prior practice to employ a large excess of the second antibody so as to achieve maximum protein precipitation. In such improved procedure it has been found that maximum counts are obtained in the precipitated conjugate when the volume ratio of second antibody to serum sample is about 1/80.

The subject conjugate is formed by a reaction which takes place in an aqueous medium at a pH of from about 6.5 to 8.5 during a period of from about 2 to 24 hours at a temperature of from about 4°–45° C. Reaction is effected by mixing serum under test with aqueous buffer, labelled antigen and second antibody. The order is not critical.

The agglutinated material obtained is filtered through a 2.4 cm Whatman GF/c filter using a Millipore manifold filter apparatus. Although the agglutinated conjugate is not visible it is retained by the filter in the above procedure. The filter is then washed well with distilled water and the label detected by counting the radioactivity.

In order to minimize nonspecific binding of antigen, it is desirable to prewash the filter. The preferred prewash medium is bovine serum albumin although other reagents, such as, human serum immunoglobulin, ovalbumin and hemoglobin may also be employed. The preferred prewash is with 0.5 ml of a solution containing 2% by weight fraction V BSA together with a chelating agent such as 0.01 M ethylenediaminotetracetic acid (EDTA).

In a further aspect of the present invention it is possible to employ an insolubilized second antibody which will serve to efficiently bring down the labelled antigen-rubella specific antibody conjugate from solution. The second antibody is insolubilized by attaching said second antibody to an insoluble support material. Suitable support materials include water insoluble organic polymeric substances such as cellulose or other polysaccharide, a vinyl addition polymer or condensation polymer or a water insoluble inorganic substance of polymeric nature, such as, glass or silicone resins or the second antibody may be absorbed to the surface of a solid support such as polystyrene, polypropylene, polyfluoroethylene or polyvinylidene fluoride. The method of attachment of the second antibody to the solid support is not narrowly critical and may include (1) covalently coupling the soluble second antibody to any insoluble polymeric substance; (2) converting the soluble second antibody to an insoluble polymerized form, such as, by reaction with an insolubitying agent; (3) physical entrapment of particles of the second antibody in the pores of a gel polymer such as a cross-linked polyacrylamide; or (4) by physical adsorption on a insoluble polymeric substance.

In a preferred embodiment of this aspect of the invention, the second antibody is supported by absorption on activated Kynar utilizing the general procedures disclosed in U.S. Pat. No. 3,843,443.

The method of the present invention is further illustrated by reference to the following Example.

EXAMPLE 1

Growth of Rubella Virus in Vero Cells

A continuous line of African green monkey kidney cells (Vero) was grown to confluency at 37° C. in glass roller bottles (500 mm length) using the following medium: Minimal Essential Medium (Eagle) with Earle's salts and containing 3.0 ml./100 ml. of 7.5% NaHCO$_3$, 10 ml./100 ml. of heat-inactivated new-born bovine serum, 1 ml./100 ml. of 200 mM glutamine and penicillin-streptomycin (100 units/ml.–100 μg/ml.).

Infection of Vero Cells with Rubella Virus

Tissue culture medium was removed from roller bottles containing confluent monolayers of Vero cells and each monolayer was washed once with phosphate buffered saline (without calcium and magnesium) pH 7.2. Stock preparations of rubella virus (strains M-33 or Gilchrist) were diluted approximately 1-50 or 1-100 in Minimal Essential Medium (Eagle) prepared as previously described with the exception that new-born bovine serum was omitted and a serum substitute consisting of 20 ng/ml. of the synthetic tripeptide glycyl-L-histidyl-L-lysine acetate were added. Thirty ml. of the diluted virus inoculum were added to each roller bottle and virus adsorption was for 1 hour at 24° C. at 2 rpm. At the end of the adsorption period, 70 ml. of Minimal Essential Medium (Eagle) containing NaHCO$_3$, glutamine, penicillin-streptomycin and the synthetic tripeptide glycyl-L-histidyl-L-lysine (as described above) were added to each rubella virus-infected monolayer. Incubation was continued at 34° C. at 1 rpm.

Concentration of Rubella Virus

Beginning on the third day after virus infection, the tissue culture fluids were removed from each roller bottle of rubella-infected Vero cells and each bottle was refed with 100 ml. of the serum free Minimal Essential Medium (Eagle) previously described. Harvesting of supernatant fluid was continued daily for an additional 8–10 days after virus infection.

Pooled supernatant fluids were clarified of cell debris by centrifugation at 5,000 rpm for 30 minutes at 4° C. Rubella virus in clarified supernatant fluids was then concentrated approximately one hundred-fold using an Amicon DC-2 hollow fiber concentrator equipped with a 10,000 molecular weight cut-off hollow fiber filter. Final concentration of virus was made in phosphate buffered saline, without calcium and magnesium, at pH 8.0. Concentrated virus was stored at −70° C.

Iodination of Rubella Virus

The following components were added to a 3.0 ml. V-vial:
1. 100 μl rubella virus (about 150 μg/ml. of protein);
2. 200 μl 0.5 M potassium phosphate, pH 7.5;
3. 20 μl $^{125}$I (5 mCi);
4. 20 μl Chloramine-T (0.5 mg./ml.)

After incubation for 1 minute at room temperature with gentle shaking, 5. 500 μl sodium bisulfite (0.1 mg./ml.) were added to the V-vial and incubation for 30 seconds at room temperature with gentle shaking was completed before addition of
6. 200 μl KI (1 mg./ml.);
7. 40 μl bovine serum albumin (10%), Fraction V.

Column Chromatography of Iodinated Rubella Virus

Iodinated rubella virus was applied to a 1×30 cm column of agarose beads (BioGel ® A-1.5 m) previously equilibrated with 0.05 M potassium phosphate, pH 7.0. Fifty fractions (1.0 ml.) were collected and the CPM of a 20 μl aliquot from each fraction was determined in a gamma scintillation counter.

Appropriate tubes comprising the first peak of radioactivity recovered from the agarose-bead column were pooled and the cpm was adjusted to 50,000/50 μl with 1% bovine serum albumin (BSA) containing 0.02 M ethylenediaminetetraacetic acid (EDTA).

Determining Optimum Dilution for Second Antibody (Goat anti-Human IgG

1. Candidate human serum (hereinafter referred to as the first antibody) was diluted 1-10 in phosphate buffered saline containing 0.1% sodium azide and was used without further treatment. This serum when treated and tested by conventional techniques in a hemagglutination inhibition (HI) test exhibited a titer in the range of 1/80 to 1/160.
2. Goat anti-human IgG (hereinafter referred to as the second antibody) was diluted from 1-10 through 1-2560 in normal goat serum (NGS).
3. Triplicate glass tubes, 12×75 mm, received the following:
  a. 100 μl PBS, pH 7.2;
  b. 5 μl first antibody (high rubella HI titer human sera);
  c. 10 μl second antibody (goat anti-human IgG diluted 1-10 to 1-2560 in NGS);
  d. 50 μl of $^{125}$I-labelled rubella Virus (hereinafter referred to as the antigen) adjusted to 50,000 CPM.
4. Glass tubes were shaken vigorously and incubated at room temperature for 4 hours.
5. Glass microfiber paper filters, 2.4 cm, (Whatman CF/C) were placed in the individual wells of a vacuum filtration system (Millipore 3025 sampling manifold). To each filter were added 500 μl of 2% BSA-0.01 M EDTA and this solution was removed by vacuum after 5 minutes.
6. The test tubes described in (3) above which contained first antibody, second antibody and antigen, received an additional 500 μl of PBS. The total volume of each tube was added to individual glass microfiber paper filters treated as described in (5) above. Fluids were removed by vacuum filtration and each filter was washed 3 times with distilled H$_2$O.
7. After the last rinse of the filters with distilled H$_2$O, each filter was removed and placed in a 12×75 mm plastic tube. The CPM/tube was determined in a gamma scintillation counter with counting time equal to 1 minute.

The results obtained in a titration of the second antibody against a constant dilution of the first antibody are shown in Table 1.

Table 1

Titration of Human Serum (First Antibody) Against Goat Anti-Human IgG (Second Antibody) Diluted from 1-10 to 1-2560 In Normal Goat Serum

| First Antibody[1] | Dilution of Goat Anti-Human IgG[2] | Average CPM |
|---|---|---|
| Rubella HI High Titer Human Serum | 1-10 | 1524 |
| | 1-20 | 1660 |
| | 1-40 | 1788 |
| | 1-80 | 1996 |
| | 1-160 | 1607 |
| | 1-320 | 1237 |
| | 1-640 | 1096 |
| | 1-1280 | 1101 |
| 1-2560 | | 883 |

From the results shown in Table 1 it can be seen that the highest average CPM was obtained with a 1-80 dilution of the second antibody against a constant dilution (1-10) of the first antibody.

Evaluation of High, Low and Negative Rubella HI Titer Human Sera by a Radioimmunoassay Procedure 1. First antibody was used having a high titer (80-160) and a low titer (10-20), said titer levels being determined by HI test as before. Additionally, a negative serum having a titer below 10 was used.
2. Goat anti-human IgG was used as second antibody diluted to 1/80 with NGS.
3. Triplicate glass test tubes, 12×75 mm, received the following:
  a. 100 μl PBS, pH 7.2;
  b. 5 μl first antibody (high, low or negative rubella HI titer human sera);
  c. 10 μl second antibody (goat anti-human IgG diluted 1/80 in NGS);
  d. 50 μl of $^{125}$I-labelled antigen adjusted to 50,000 CPM.
4. Glass tubes were shaken vigorously and incubated at room temperature for four hours.
5. Test specimens were added to glass microfiber paper filters and radioactivity (CPM) was determined as previously described in paragraphs (5), (6) and (7) of the section *Determining Optimum Dilution for Second Antibody (Goat anti-human IgG)*.
6. The results, expressed as average CPM, obtained in such a radioimmunoassay procedure as described herein with human sera of known HI titer are shown in Table 2.

Table 2

Use of a Radioimmunoassay Procedure to Detect Antibody to Rubella Virus in Human Sera of Known Hemagglutination-Inhibition Titer.

| HI Titer of Human Serum[1] | Average CPM |
|---|---|
| High (80-160) | 3036 |
| Low (10-20) | 1857 |
| Negative (<10) | 1584 |

[1]Diluted 1-10 in PBS.

From the results shown in Table 2 it can be seen that the average CPM was proportional to the HI titer of the test serum. For example, a high titer serum (HI titer 80-160) had an average CPM of 3036, a low titer serum (HI titer of 10-20) had an average CPM of 1857 and a negative titer serum (HI titer <10) had an average CPM of 1584. By constructing 95% confidence intervals the following standards were obtained: (1) for a test serum to have a HI titer of 80-160 the CPM must be at least 2378 and (2) for a test serum to have a HI titer of 10-20 the CPM must be at least 1678. Any test serum with a CPM less than 1678 would be considered to have a HI titer of less than 10 and therefore would be considered a negative.

Stability of $^{125}$I-Labelled Rubella Virus

Following iodination of rubella virus, the radioactivity was adjusted to 50,000 CPM/50 μl by dilution of the antigen in 1% BSA containing 0.02 M EDTA. The antigen was stored at 4° C. and performed satisfactorily for a period of 4 weeks.

We claim:
1. $^{125}$I-rubella virus.
2. In an immunoassay for determining the presence of rubella virus specific antibodies in human serum which comprises the steps of:
  A. Providing a reaction mixture comprising a buffered aqueous medium; human serum to be assayed; antigen derived from rubella virus and a second antibody specific to human IgG;
  B. Incubating said reaction mixture to form an antigen-antibody-second antibody conjugate when said rubella virus specific antibody is present in said serum sample, said conjugate bearing a detectable label; and

C. Determining the level of said label as a measure of the presence of said antigen-antibody-second antibody conjugate and correlating said level against a standard curve to determine whether positive levels of said rubella virus specific antibody were present in said serum sample;

the improvement which comprises utilizing $^{125}$I-rubella virus as the antigen.

3. The improved immunoassay of claim 2 wherein said second antibody is goat anti-human IgG.

4. The improved immunoassay of claim 2 wherein said reaction buffered aqueous medium comprises phosphate buffered saline, pH 7.2.

5. The improved immunoassay of claim 2 wherein the $^{125}$I-rubella virus antigen is adjusted to 50,000 CPM prior to addition to said reaction mixture.

* * * * *